(12) United States Patent
Sahl

(10) Patent No.: US 7,014,676 B2
(45) Date of Patent: Mar. 21, 2006

(54) METHOD OF CONVERTING WASTE TO SOIL/FEED MODIFIERS

(75) Inventor: Helge Otto Friedrich Sahl, Muncie, IN (US)

(73) Assignee: Global Solutions, LLC, San Diego, CA (US)

( * ) Notice: Subject to any disclaimer, the term of this patent is extended or adjusted under 35 U.S.C. 154(b) by 0 days.

(21) Appl. No.: 10/617,265

(22) Filed: Jul. 8, 2003

(65) Prior Publication Data

US 2005/0247090 A1 Nov. 10, 2005

Related U.S. Application Data

(60) Provisional application No. 60/394,384, filed on Jul. 8, 2002.

(51) Int. Cl.
 *C05F 9/00* (2006.01)
(52) U.S. Cl. ............................ 71/14; 71/6; 71/8
(58) Field of Classification Search ............ 71/6, 71/8, 14
 See application file for complete search history.

(56) References Cited

U.S. PATENT DOCUMENTS

| | | | |
|---|---|---|---|
| 3,655,046 A | 4/1972 | Trussell | 210/610 |
| 3,736,120 A | 5/1973 | Tempe | 71/9 |
| 3,756,784 A | 9/1973 | Pittwood | 422/194 |
| 3,847,803 A | 11/1974 | Fisk | 210/18 |
| 3,934,999 A | 1/1976 | Meier | 71/9 |
| 4,032,318 A | 6/1977 | Lovness | 71/9 |
| 4,053,394 A | 10/1977 | Fisk | 210/8 |
| 4,132,638 A | 1/1979 | Carlsson | 210/9 |
| 4,267,049 A | 5/1981 | Erickson et al. | 210/606 |
| 4,342,650 A | 8/1982 | Erickson et al. | 210/606 |
| 4,869,877 A | 9/1989 | Sellew et al. | 435/290.2 |
| 4,956,002 A | 9/1990 | Egarian | 71/9 |
| 5,269,829 A | 12/1993 | Meyer | 71/9 |
| 5,326,477 A | 7/1994 | Fugua et al. | 210/632 |
| 5,380,445 A | 1/1995 | Rivard et al. | 210/748 |
| 5,441,552 A | 8/1995 | DeLillo | 71/9 |
| 5,527,464 A | 6/1996 | Bartha et al. | 210/603 |
| 5,531,898 A | 7/1996 | Wickham | 210/606 |
| 5,670,047 A | 9/1997 | Burke | 210/603 |
| 5,709,796 A | 1/1998 | Fuqua et al. | 210/632 |
| 5,744,041 A | 4/1998 | Grove | 210/602 |
| 5,810,903 A | 9/1998 | Branconnier et al. | 71/9 |
| 5,846,425 A | 12/1998 | Whiteman | 210/606 |
| 5,849,566 A | 12/1998 | Dale et al. | 435/262 |
| 5,879,928 A | 3/1999 | Dale et al. | 435/264 |
| 6,077,704 A | 6/2000 | Vanderberg et al. | 435/262.5 |
| 6,083,395 A | 7/2000 | Katsura et al. | 210/606 |
| 6,197,081 B1 * | 3/2001 | Schmidt | 71/1 |
| 6,224,646 B1 | 5/2001 | Arato et al. | 71/9 |
| 6,224,769 B1 | 5/2001 | Hasegawa et al. | 210/606 |

FOREIGN PATENT DOCUMENTS

| | | | |
|---|---|---|---|
| BE | 879840 | * | 3/1980 |
| JP | 54064073 | * | 5/1979 |

* cited by examiner

*Primary Examiner*—C. Sayala
(74) *Attorney, Agent, or Firm*—Holland & Knight LLP

(57) ABSTRACT

Disclosed is a method for transforming Municipal Solid Waste (MSW) into a useful compost material. The method involves both a pre-treatment and a treatment phase. In the pre-treatment phase, a waste stream is processed to remove valuable waste after which the waste is ground to a suitable size. In the treatment phase, heat and pressure are applied to the waste and activators are added to sterilize the waste and transform it into a useful end product.

2 Claims, 3 Drawing Sheets

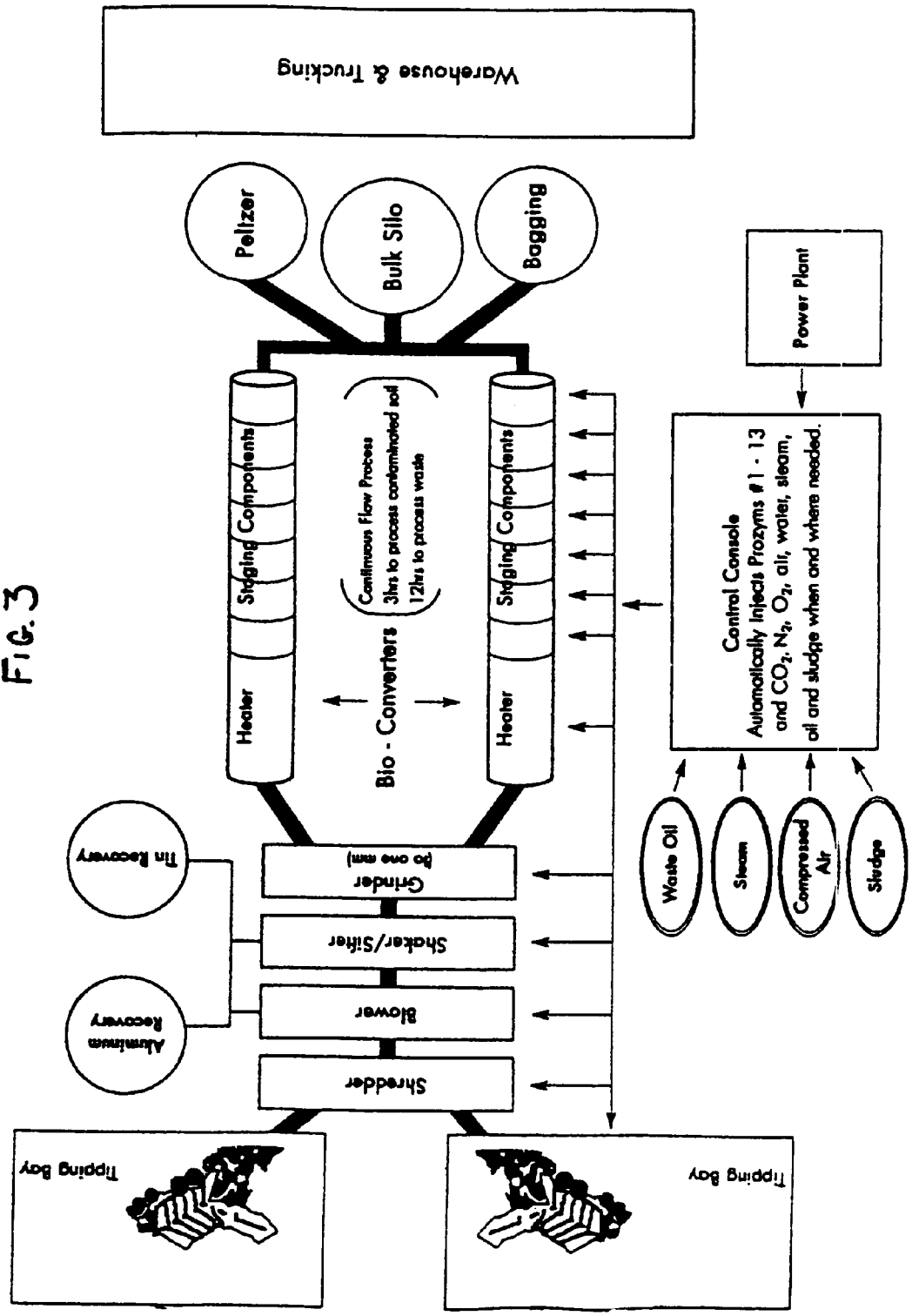

METHOD OF CONVERTING WASTE TO SOIL/FEED MODIFIERS

RELATED APPLICATION DATA

This application claims benefit of provisional application 60/394,384 filed on Jul. 8, 2002 entitled Method of Converting Municipal Solid Waste to Useful Compost Material. The contents of this provisional application are incorporated herein by reference.

BACKGROUND OF THE INVENTION

1. Field of the Invention

This invention relates to a method of transforming various waste streams—municipal, industrial, sewage, animal, chemical, medical, contaminated and toxic waste—into enriched soil, fertilizers, mulch, animal/fish feeds and other products (i.e. municipal solid waste into useful compost materials). More particularly, the present invention relates to transforming municipal solid waste into an organic product by way of thermo and bio-chemical activators, within a period of 3–24 hours, depending on the waste stream being processes. These waste streams can be processed all together or separately or in combinations to affect the desired outcome and end product.

2. Description of the Background Art

Presently, the aerobic degradation of waste materials is known in the art. This degradation is employed in converting waste materials into useful products such as fertilizer. However, all the following processes while having some similarities in their methods and process, have one very significant drawback: none of the methods claim to process all waste, all together. Rather, all the prior art requires some sorting or specialized waste streams. Sorting in the method of the present invention is optional. Also, all these methods take no less than 10 days, and some up to 4+ weeks to produce their end product.

For example, U.S. Pat. No. 4,132,638 to Carlsson relates to a process for the aerobic degradation of waste materials, such as water sludge from municipal waste water treatment plants. The method of Carlsson first grinds degradable substances to a particle size of at most 50 mm and preferably less than 10 mm and then mixes the finely ground material with water to produce a slurry. Enzymes are then added to promote degradation and the slurry is preheated to 40° to 80° C. The final compost product can be dewatered and palletized for use as a fertilizer. The degradation process requires a 10 day period of time.

U.S. Pat. No. 5,326,477 to Fugua et al. discloses the addition of various enzymes to solid waste to breakdown different waste components. The process is employed upon solid wastes such as absorption pads (e.g. diapers).

U.S. Pat. No. 3,736,120 to Tempe describes a waste treatment process in which solid refuse material is first sorted to remove non-degradable materials. The organic portion of the waste is mixed with sewage, sludge and ground. After grinding, enzymes are added. The material is subjected to aerobic fermentation with agitation and addition of different types of bacteria.

U.S. Pat. No. 3,934,999 to Meier describes a home composting process in which organic waste materials are placed in a perforated plastic bag. A composting tablet is added to the bag. The tablet contains enzymes that accelerate the activity of the microorganisms. The process requires a 4 to 6 week time period.

U.S. Pat. No. 4,032,318 to Lovness discloses a composting mixture to promote decomposition of organic materials. The mixture includes enzymes to breakdown the cell structure of the organic material and promote the activity of the microorganisms.

U.S. Pat. No. 4,267,049 to Erikson et al. describes a process for treating raw municipal waste waters and includes the steps of initially adding hydrolytic enzymes. Heavy metals may be removed with a chelating step. The final material may be used as a fertilizer.

Finally, U.S. Pat. Nos. 3,847,803 and 4,053,394 to Fisk describe a process for treating raw sewage and solid waste in which the material is first ground and anaerobically fermented. The resultant material is sterilized. Bacteria and enzymes are then added and the material is aerobically fermented.

Although each of the above referenced inventions achieves its individual objective, they all suffer from common drawbacks. Namely, none of the prior methods discloses a system for effectively treating combinations of all waste, or selective waste streams of both organic and non organic waste, or an entire municipal waste stream.

Moreover, none of the prior methods disclose using a pressurized high temperature sealed environment for the purposes of sterilization. All of the methods use enzymes, but what is different is the order in which the enzymes are introduced and the manner in which these enzymes are used in combinations with other organic digesting accelerants, bio-activators, chelators and thermoactivators (and the combinations of enzyme chelators thermoactivators to promote decomposition of a waste mixture). Finally, all the prior art methods involve extended processing periods, typically 10 days (48 hours) or more.

SUMMARY OF THE INVENTION

It is therefore one of the objectives of this invention to provide a method for converting an entire waste stream into a useful organic product.

It is also an object of this invention to utilize a sealed and pressurized vessel in sterilizing a waste stream.

Still another object of this invention is to use both a mechanical and a chemical process to convert varied waste streams in combination or separate, or organic and non organic waste into an organic end product.

These and other objectives are accomplished by providing a system which has a pretreatment phase wherein an enzyme solvent and deoderizer is first sprayed onto raw waste prior to it being ground and shredded by way of a mechanical grinding process and further broken down by way of a reagent solution. Thereafter, the waste stream is treated by the addition of a manure and/or sludge, lime and sand. A nutrigenic enzyme thermoactivator is then added to the mixture. The resulting mixture is then heated and pressurized in the drum for purposes of sterilization. This ground waste is then heated in a rotating sealed drum for a period of time. Once the cooking phase is complete the vessels is opened and continues to rotate. Once the material cools to approximately 50 C. the first of one to five different combinations of enzyme bioactivators and oxigen are introduced as needed to accelerate the degredations process. The first in this phase is a stabilized post-pressure biological starter solution that is added to further decompose the mixture. Thereafter, an additional thermo bio-chemical enzyme activator is added to the solution along with oxygen while the vessel continues to rotate. It is a critical part of this process that the drum continue to rotate as this stimulates the degredation process. Finally, a solubilized starch polysaccharide solution is added to the mixture. The resulting mixture is then ready for use as a fertilizer, mulch, animal/fish food.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 3 is a schematic representation of the present invention.

Similar reference characters refer to similar parts throughout the several views of the drawings.

DETAILED DESCRIPTION OF THE PREFERRED EMBODIMENT

Figure 1:
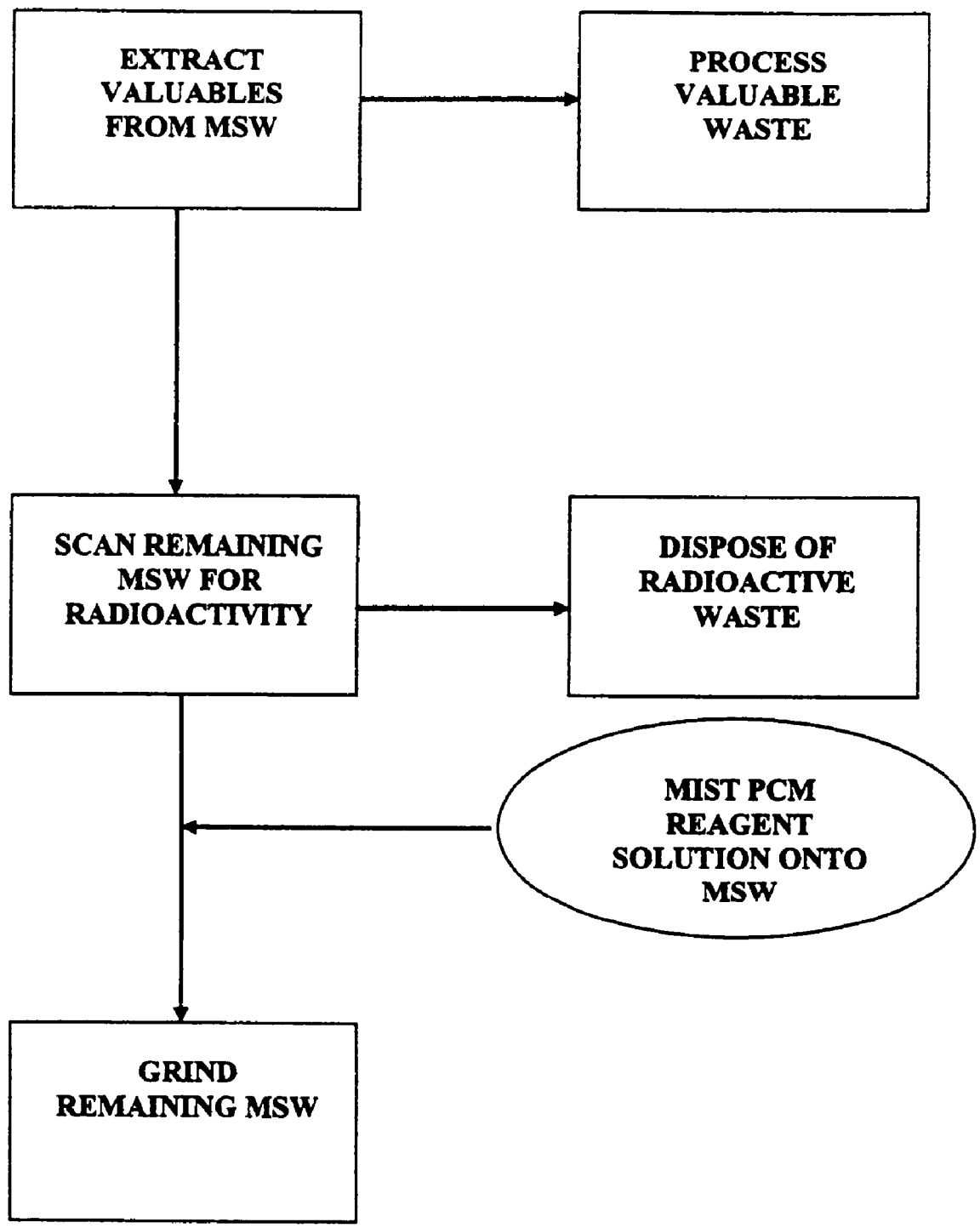
FIG. 1 is a flow chart showing the pretreatment steps of the method of the present invention with the mechanical steps being shown as rectangles and the chemical steps being shown as ovals.

The present invention relates to a method whereby waste or—municipal solid waste ("MSW"), such as paper, industrial, sewage, medical toxic, animal, organic and non-organic waste can be converted into enriched soil, fertilizer, mulch, animal/fish feed and other products. The method employs a combination of mechanical and chemical steps carried out in both a pre-treatment and treatment phase. In the pretreatment phase, the waste is brought into a form and size suitable for subsequent treatment. Solids are ground to 1 mm and combined with the liquid waste streams. In the treatment phase, the ground waste is processed via heating, pressurization, and the addition of various reagents to create the useful end product. In general, the present method can be visualized as a giant digestion process that returns waste into its organic and useful cellulose state.

The waste that can be treated in accordance with the present invention includes organic and non-organic waste: animal waste/parts, sewage, batteries, tires, rubbers, metals, aluminum, tin, glass, all paper products, magazines, card board, plastics of all kinds (hard to soft), contaminated soils, oil, grease, gasolines, paint, computer, printers, cartridges, televisions, concrete, incinerator ash, pesticides, benzene, PCB's, carcinogens, medical waste/needles, medicines/chemicals/body parts. Whole tires are either processed separately or are shredded and then added at a controlled percentage to the whole waste stream. Of course, organic materials can also be separately processed by the method of the present invention and will produce animal/fish feed with a processing time of 3–8 hours. These organic materials can include such things as: wood, yard waste, food waste, cooking oil/grease, card board, paper, sewage, animal waste and parts. The system can also be used in processing contaminated soils. Here, the soil can be added to the whole waste stream for processing; alternatively, the soil can be processed separately in approximately 2–3 hours.

The only limitation regarding the waste that can be processed with this method is that it is capable of being ground during the pre-treatment phase. This, in turn, is a function of the size of the waste stream and the capability of the grinding equipment used. Should extremely large parts be employed with the method, such as large metallic components, they can first be shaved down to a grindable size and then returned to the waste stream. Other wastes that require limits on a percentage to whole waste stream are batteries, metals and toxins/contaminants and water/moisture.

In an important aspect of the present invention, there are no harmful emissions from the waste stream during processing. Specifically, no arsenic or harmful emissions are produced. Steam produced during the method is either reintroduced into the processing stream or it is converted to liquid and then added to the processing stream. Computerized exhaust sensors are used to monitor the steam to ensure no toxins are produced. If elevated levels of toxins are detected the level of neutralizers and/or sterilizers can be added to break down the toxins.

Methane is produced by the system but is reintroduced into the waste stream during processing and converts to Nitrates in the final material. Some of the potential uses of the end product include fertilizers, nutroponic soil, mulch, animal feeds, fish foods, and a combustible "brown coal" products. The various aspects of the method of the present invention are described in greater detail hereinafter.

Pre-Treatment Steps

With reference now to FIG. 1 the pretreatment steps of the present invention are depicted. In the flow chart of FIG. 1 the mechanical steps of the pretreatment phase are indicated as rectangles whereas the chemical step is indicated as an oval. Thus, as disclosed, the pretreatment phase of the method includes a combination of mechanical and chemical steps. The first step in the process is to automatically extract valuable materials from the waste stream. For example, materials such as aluminum cans can be extracted depending upon their economic value at the time. This extracted valuable waste material can then be processed in accordance with standard techniques to realize the value of such selected waste material.

Thereafter the remaining waste is scanned by way of a conventional Geiger counter or other radioactive detection system to ascertain whether the remaining waste contains any radioactive materials. If any radioactive materials are discovered they are disposed of in a subsequent step in accordance with all appropriate state and municipal regulations. It is expected that the method could easily handle waste with radio active percentages of between 1%–4%.

Next, the remaining waste is misted prior to being conveyed to a grinding step. More specifically, an enzyme solvent deoderizing solution (PCM) is misted onto the waste. In the preferred embodiment this mist is delivered via nozzles at a pressure of 5 pounds per square inch (PSI).

Thereafter, the waste with the added PCM reagent is transferred to the grinding station. This grinding process can be achieved by known apparatuses with the objective of reducing the size of the waste particles to 1 millimeter or less. It has been found that this waste particle size is best suited for subsequent mechanical and chemical processing during the treatment phase of the method.

Treatment Steps

Next, the treatment phase is carried out on the waste particles. In the first step of this phase, the ground waste is transferred to a kettle or drum that is sealed in such a manner as to keep the contents under pressure. The drum is also rotatable to allow for mixing of its contents. Spurge lines and controls are included for selectively adding materials to the drum at various times during the process as needed.

The following items are added to the ground waste before the drum is sealed: 1 lb per ton of manure and/or sludge/or food grade Urea, 1 lb per ton of stable lime, and 20 lbs per ton of rough coarse sand. The nature of the manure and/or sludge added depends upon the characteristics of the waste being treated. These additives combined with the original PCM activate the first chemical step of the treatment.

In the next step, the drum is heated and pressurized by the addition of steam. Nitrogen can also be added to assist in sterilization. The steam is added through a center spurge line and is sufficient to pressurize the contents of the drum or drum, and raise the temperature of the contents to 120° C. This temperature is maintained for approximately 37 minutes in the preferred embodiment, which has been found to be a sufficient length of time to completely sterilize even the most dangerous toxic wastes present in a waste stream. During the heating and pressurization, rotation of the drum is maintained to continually mix the contents and to assure a uniform heating. As it is rotated, air is infused into the drum through the center spurge lines.

Figure 2:
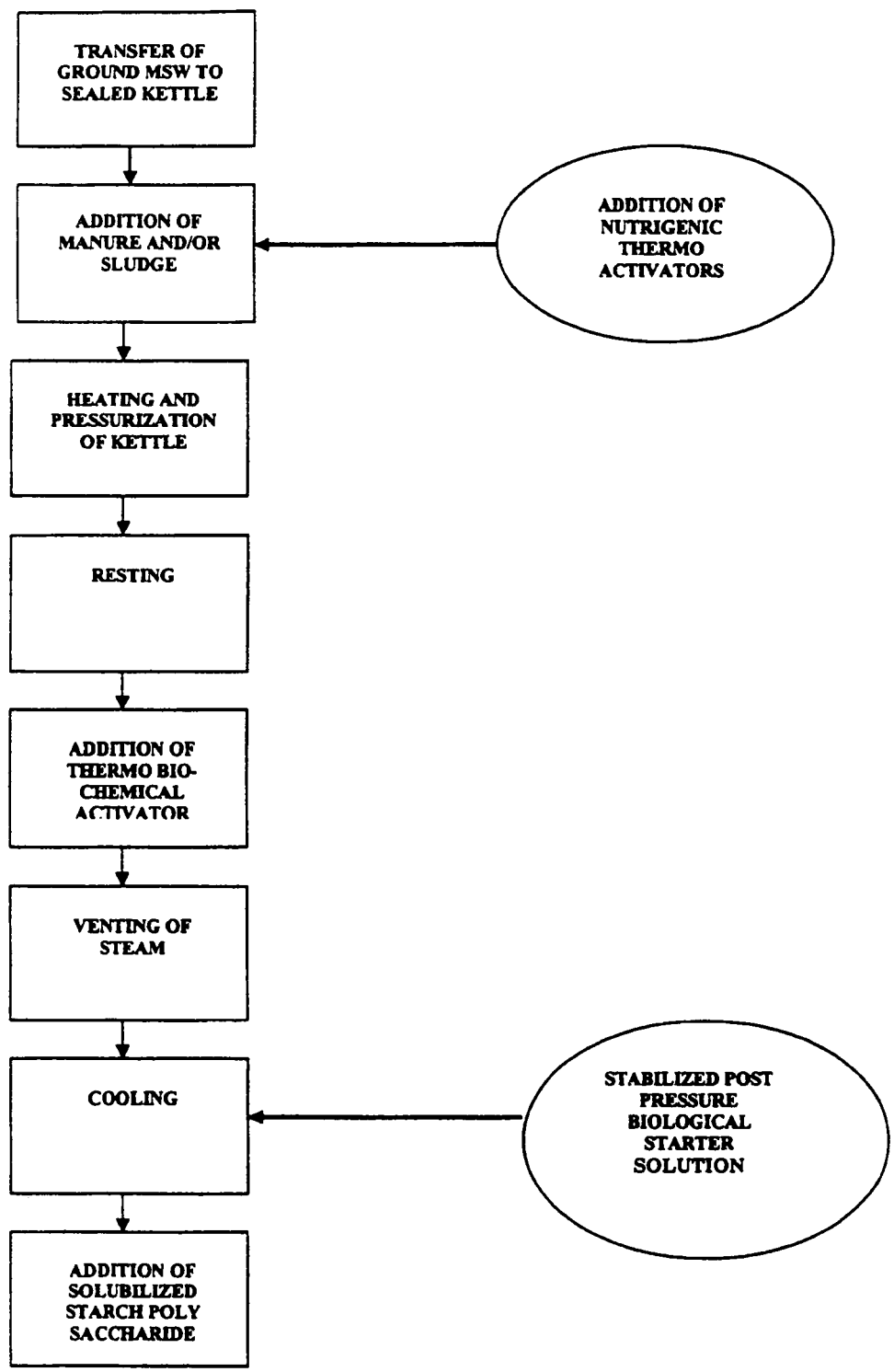
FIG. 2 is a flow chart showing the treatment steps of the method of the present invention with the rectangles showing the mechanical steps and the ovals showing the chemical steps.

Next, a resting period is initiated. During the resting period, which ideally lasts between 10 to 30 minutes, heating is abated to a temperature of 50 C. After the resting period an additional chemical step is carried out. Specifically, a nutrigenic thermoactivator is added to the contents of the drum by way of a spurge line. This thermoactivator is an enzymatic solution that is used in degrading the waste. The thermoactivators are mixed with the waste by rotating the drum. Specifically, as illustrated in FIG. 2, the first of 1–5 thermo bio activator enzyme solutions is added to the drum via a center spurge line. This activator, which can again take the form of an enzymatic solution, functions in degrading the waste at the cellular level. During the addition of the thermo bio-activator enzymes, the drum is continually rotated and oxygen (at ¼ lb per ton per 1–3 hours) is infused at regular intervals. In the preferred embodiment, the drum is rotated at a speed of 3 rpm and infused with air at 5 to 30 minute intervals.

With continuing reference to FIG. 2, the next step of the treatment phase is depicted. Separate organic material generally completes processing with only one application of bio-activators enzymes, while non-organic and contaminated waste streams may need 4–5 applications of the thermo bio-activators enzymes. Specifically, as illustrated in FIG. 2, a stabilized post pressure biological starter solution is added, again via a center spurge line. This post pressure starter solution is an enzymatic solution that is adapted to further the breakdown of the waste. Thereafter, in the final chemical step of the present invention, a solubilized starch polysaccharide solution is added via a spurge line. This has the effect of sustaining the biological reaction started by the biological starter solution. Appropriate stabilizers can be added as required.

The entire bio-conversion process is typically completed in 3 to 6 hours for an organic waste stream. For whole waste streams, including both organic and inorganic materials, this time is increased to between 6–24 hours. The time it takes to reach this point depends on the composition of the waste stream. Both these process times are a significant advancement over prior art methods. It has been found that these time frames are sufficient to appropriately heat the materials and degrade them by way of thermal activators and reagents to achieve the desired characteristics in the end product.

It should also be noted that additives, digesters, enzymes, sulfur, minerals, and/or nutrients added to the waste stream during the steps of the present invention depend upon whether the waste stream is organic or inorganic. With organic waste, such as animal waste, there is a much shorter processing time and feeders, enzymes, digesters and nutrients are only added at four times at certain intervals throughout the process. By contrast, with whole waste streams feeders, enzymes and digesters are introduced nine times throughout the method. That is, the number of additions for a typical whole waste stream is: emulsifiers (1); neutralizer/sterilizer (1); digesters (1–5); and enrichers/nitrients (1–2). The resulting processes, however, is the same for both purely organic and whole waste streams. The total formulas added amounts to approximately one gallon of enzymes per ton.

With reference to FIG. 3 an additional schematic of the conversion system is depicted. As illustrated in FIG. 3, the waste is brought into the system by way of conventional garbage trucks and a tipping bay. This waste stream is then processed to recover valuable materials such as aluminum and/or tin. The remaining waste is then shredded, blown, shaken, sifted, and ground to achieve the appropriate particle size for further bio-conversion steps. As indicated, the bio-converter steps take place at various stages under the application of heat. Also as depicted, a control console is employed to automatically add the appropriate reagents or prozyms at the various required stages. As illustrated by the ovals in FIGS. 1 and 2, the staging components, heat, and prozyms are all employed to achieve the resultant desired end product, which can be palletized, stored in a bulk silo, or bagged as indicated in FIG. 3.

There are many, many end products which can be achieved by the conversion method of the present invention. The end product that is achieved is a function of both of the type of waste that is introduced into the system as well as the various thermoactivators and/or reagents that are added during the chemical steps. Some of the end product classifications are: fertilizers of various formulations; nutriponic soils; high grade mulch; animal and fish food.

The entire method can be carried out by way of a portable apparatus. This enables the system to be transported to various job sites for the processing of waste. The system can also be used on cruise or military ships. The systems is also inexpensive to build such that it can be used by individuals and in rural areas such as farms.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention. Now that the invention has been described,

What is claimed is:

1. A method of converting municipal solid waste into a useful compost material, the method comprising the following steps:
   providing a stream of solid waste for treatment, including both inorganic and organic materials;
   grinding the solid waste into particles;
   transferring the ground solid waste into a drum;
   adding manure and/or sludge to the drum and thereafter sealing the drum;
   rotating the drum to mix the ground solid waste, manure and/or sludge;
   sterilizing the contents of the drum by adding steam;
   permitting the drum to cool and thereafter depressurizing the drum by venting the remaining steam;
   removing the contents of the drum;
   wherein the bioconversion of whole waste streams can be completed within a 24 hour period; and wherein the method converts both organic and inorganic materials into useful compost material
   wherein prior to grinding the solid waste it is scanned with a Geiger counter to detect the presence or absence of radioactive materials and wherein any detected radioactive materials are removed from the solid waste.

2. A method of converting municipal solid waste into a useful compost material, the method comprising the following steps:
   providing a stream of solid waste for treatment;
   grinding the solid waste into particles;
   transferring the ground solid waste into a drum;
   adding manure and/or sludge to the drum and thereafter sealing the drum;
   rotating the drum to mix the ground solid waste, manure and/or sludge;
   sterilizing the contents of the drum by adding steam;
   permitting the drum to cool and thereafter depressurizing the drum by venting the remaining steam;
   removing the contents of the drum; and
   wherein prior to grinding the solid waste it is scanned with a Geiger counter to detect the presence or absence of radioactive materials and wherein any detected radioactive materials are removed from the solid waste.

* * * * *